No. 12,817. REISSUED JUNE 16, 1908.

H. S. COVER.

EYE GUARD.

APPLICATION FILED MAR. 23, 1908.

Witnesses.
Edward T. Wray.
Sophie B. Wolner.

Inventor.
Harvey S. Cover.
by Parker Carter
Attorneys.

UNITED STATES PATENT OFFICE.

HARVEY S. COVER, OF SOUTH BEND, INDIANA.

EYE-GUARD.

No. 12,817. Specification of Reissued Letters Patent. Reissued June 16, 1908.

Original No. 850,997, dated April 23, 1907, Serial No. 346,258. Application for reissue filed March 23, 1908. Serial No. 422,867.

*To all whom it may concern:*

Be it known that I, HARVEY S. COVER, a citizen of the United States, residing at South Bend, in the county of St. Joseph and State of Indiana, have invented certain new and useful Improvements in Eye-Guards, of which the following is a full, clear, and exact specification.

This invention relates to new and useful improvements in eye guards or shields for firemen, metal-workers, chauffeurs, and others who are likely to be subjected to the action of fumes, gases, wind, grit, dust, etc.

The invention consists in providing an eye-guard of a single piece of material provided with two lens-holding portions connected by the same member that forms the cushioning part of the guard.

Another object resides in the provision of integral or other reinforcing ribs or elements between the lens-holding members and the cushioning part of the guard to prevent the lens-holding portions springing back and partially obscuring the sight when a pull is exerted upon the head-gear.

A still further object is to obviate the use of cement or other fillings between the lenses and the lens-holding portions.

It is still further designed to eliminate the connection of the ears and a bridge-piece to the lens-holding portions proper, but, on the other hand, to provide for the connection of the ears and bridge-piece connections at a distance somewhat remote from the connection of the lenses with the lens-holding portions and with respect to the lens-holding portions themselves. By reason of this peculiar disposition of the ears and nose-piece with respect to the lens-holding portions both of the ears and nose-piece perform not only their usual function, but also act as cushioning members.

Figure 1:
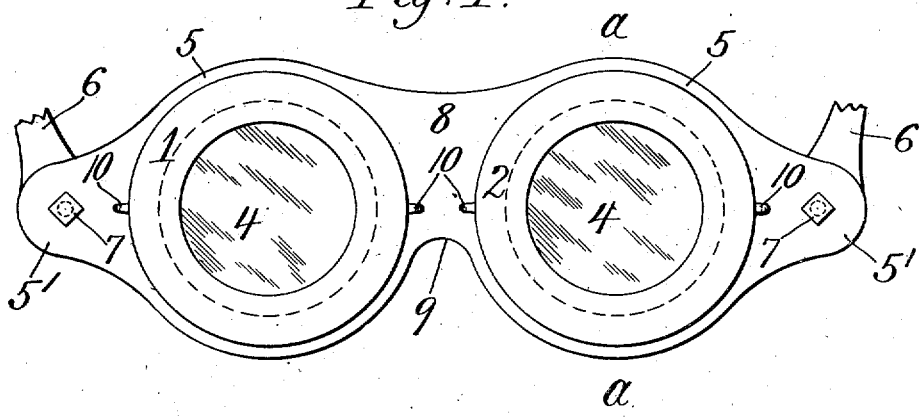
Figure 2:
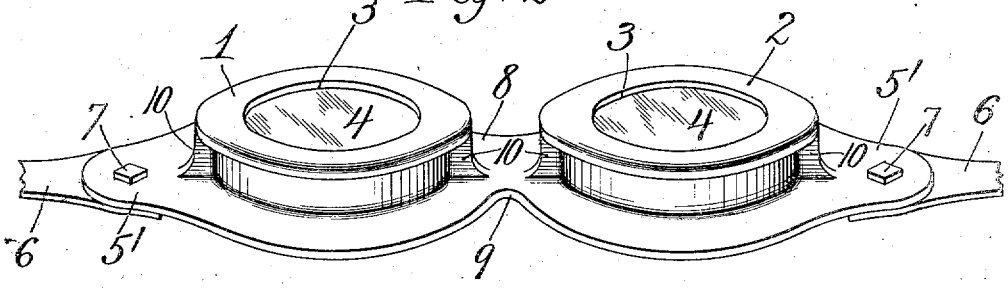
Figure 3:
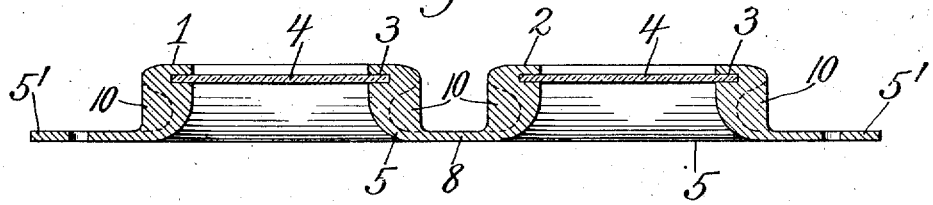
Figure 4:
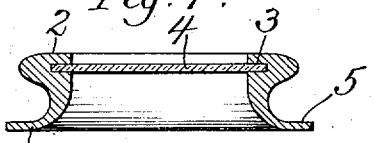

In the drawings, Figure 1 is a face view of the invention. Fig. 2 is an edge view. Fig. 3 is a longitudinal sectional view, and Fig. 4 is a section taken through Fig. 1.

Referring more particularly to the accompanying drawings, the reference characters 1 and 2 indicate the lens-holding portions of my improved guard, each having an annular recess 3 near its outer end for the reception of the peripheral edges of the corresponding lenses 4. These lens-holding portions each taper rearwardly or downwardly, gradually decreasing in thickness to their flaring edges, the flaring edges 5 being designed to possess such flexibility as to assume proper positions upon the wear to fit the orbits of the eyes, regardless of any distortions or wrinklings of the face, due to fumes, gases, grit, wind, dust, etc. These flaring portions 5 terminate adjacent the outer ends of the lens-holding portions 1 to provide the ears 5′, to which latter may be secured the head-bands 6 by means of a suitable fastening 7. Adjacent the inner opposite sides of the lens-holding portions 1 this flaring portion of the lens-holding portions forms a connecting web portion 8 at the base of the lens-holding portions. This web portion 8 forms the nose-bridge and is provided in its edge with a recess 9, designed to fit the nose of the wearer.

From the description thus given it will be seen that the nose-piece 8 is formed at the base, or, in other words, at the inner or rear parts of the lens-holding portions instead of directly across the lens-holding portions at their outer faces. In the present instance the nose-piece is of comparatively thin material, permitting of a doubling or folding of one lens-holding portion upon the other, so that the guard may require but little space and whereby the guard may be conveniently carried in one's pocket. The gradually-tapering portions of the lens-holding members, including the nose-bridge part, form the cushion of the guard, the flaring parts extending beyond the peripheries of the lens-holding parts, as shown.

The character 10 indicates ribs formed integrally with the body of the guard and designed to prevent the lens-holding portions from bending out of shape and partially obscuring the sight when a pull is exerted by the head-bands 6. These ribs prevent the greater part of the pull by the head-bands upon the flaring or cushioned members being transmitted to the lens-holding portions, thus rendering unnecessary the use of means other than the flaring or cushioning parts to hold the lenses in their seats in the lens-holding members. It will thus be understood that the use of cement, fillings, etc., between the lenses and lens-holding portions is obviated.

I claim:

1. An eye-guard comprising a cushion member including integral, outwardly-extending annular walls forming a pair of lens-holding portions, and integral reinforcing-ribs joining the walls of the lens-holding portions and the cushion member.

2. An eye-guard composed of a single piece of material and comprising a pair of lens-holding members whose walls taper gradually and flare outwardly to form a cushion and a nose-piece for the eye-guard, and ribs formed integrally with the walls of the lens-holding members.

3. An eye-guard comprising a cushion member having integral lens-holding portions extending outwardly therefrom and reinforcing-ribs on the lens-portions.

4. An eye-guard comprising an elastic cushion member having integral lens portions extending from one side thereof, integral ribs on the walls of said lense portions to reinforce the same, substantially as described.

5. An eye-guard consisting of two lenses, an elastic piece embodying two lens-holding portions, each consisting of a ring of elastic material, adapted to constrictively hold one lens, a flat flexible annular cushion adapted to bear upon the flesh of the wearer about the eye, a thin compressible and elastic tubular flange connecting the ring and the cushion, and a flexible bridge connecting the two flat annular cushions which bear upon the flesh of the wearer.

In testimony whereof I have signed my name to this specification in the presence of two subscribing witnesses.

HARVEY S. COVER.

Witnesses:
SOPHIE B. WERNER,
MINNIE M. LINDENAN.